United States Patent [19]

Nyzen

[11] Patent Number: 5,533,090

[45] Date of Patent: Jul. 2, 1996

[54] APPARATUS FOR ADJUSTING AND ALIGNING THE POSITION OF X-RAY EQUIPMENT

[76] Inventor: Richard C. Nyzen, 620 Merriman Rd., Akron, Ohio 44303

[21] Appl. No.: 335,165

[22] Filed: Nov. 7, 1994

[51] Int. Cl.[6] .................................................. H05G 1/02
[52] U.S. Cl. .................................... 378/197; 378/167
[58] Field of Search ........................... 378/167, 168, 378/169, 170, 177, 180, 193, 195, 196, 197, 204, 205, 206, 207, 38, 39

[56] References Cited

U.S. PATENT DOCUMENTS

| | | | |
|---|---|---|---|
| 3,492,482 | 1/1970 | Forsyth | 378/197 X |
| 3,668,392 | 6/1972 | Bajek et al. | |
| 3,790,803 | 2/1974 | Phillips | 378/206 |
| 4,002,915 | 1/1977 | Weiss et al. | |
| 4,092,544 | 5/1978 | Grim | 378/206 |
| 4,246,486 | 1/1981 | Madsen | 378/206 |
| 4,255,657 | 3/1981 | Lescrenier | 378/206 |
| 5,023,899 | 6/1991 | Ohlson | 378/197 X |
| 5,067,144 | 11/1991 | Aitkenhead et al. | 378/145 X |

FOREIGN PATENT DOCUMENTS

| 740658 | 10/1943 | Germany | 378/196 |
|---|---|---|---|

OTHER PUBLICATIONS

"The PC-1000/Laser 1000 Pan/Ceph Combination", Panoramic Corporation 4321 Goshen Rd., Fort Wayne, IN 46818 No date.

"Olympic Controls New Modular X-Ray System", Olympic Controls Corp. Fax News Letter, Nov. 26, 1991.

"Instrumentarium Imaging", Instrumentarium Imaging, Inc., 300 W. Edgerton Ave., Milwaukee, WI 53207 No date.

The MDS Ultra-Ceph, Mid∝American Dental Specialties, Inc., P.O. Box 1975, Hickory Hills, IL 60455 No date.

*Primary Examiner*—David P. Porta
*Attorney, Agent, or Firm*—Renner, Kenner, Greive, Bobak, Taylor & Weber

[57] ABSTRACT

A wall-mounted x-ray system (10) includes a pair of parallel, spaced tracks (11, 12) mounted on a wall and capable of receiving, through either of their open ends (35, 36), traveller assemblies (13, 14). One traveller assembly (13) carries an x-ray tube (18) for the x-ray source and the other traveller assembly (14) carries x-ray receiving and patient locating equipment (16). The traveller assemblies (13, 14) are moveable on the tracks (11, 12), which movement is assisted by handles (42). Handles (42) are threaded into traveller assemblies (13, 14) and when the desired position along tracks (11, 12) is reached, by tightening the handles (42) the tracks (11, 12) are engaged to hold the traveller assemblies (13, 14) in place. Traveller assembly (14) is first properly positioned relative to the patient and then traveller assembly (13) is aligned with traveller assembly (14) by use of an optical transmitter (45) carried by traveller assembly (13) and a receiving target (47) carried by traveller assembly (14).

20 Claims, 3 Drawing Sheets

APPARATUS FOR ADJUSTING AND ALIGNING THE POSITION OF X-RAY EQUIPMENT

TECHNICAL FIELD

This invention relates to an apparatus for adjusting the vertical height of wall-mounted x-ray equipment such as used by doctors and dentists. More particularly, this invention relates to such a device which also aligns the x-ray source with the film. Most specifically, this invention is best suited to be used for cephalometric x-rays.

BACKGROUND ART

When x-rays are to be taken, for example, in a doctor's or dentist's office, the alignment of the x-ray equipment and the adjustment thereof to correspond to the position or location of the patient's anatomy to be x-rayed is critical. For example, for cephalometric x-rays utilized by both doctors and dentists, the patient's head must be precisely aligned between the x-ray source and the film, and the source and the film must be aligned and separated by approximately five feet.

A problem occurs, of course, because patients are obviously of different heights. Thus, in one known cephalometric x-ray machine, a large arm of at least five feet in length is motorized and is vertically movably mounted on a wall. Near one end of the arm, the film holder and a head holding device extend laterally into the room. Near the other end of the arm, an x-ray tube holder likewise extends laterally outwardly into the room. The patient merely stands adjacent to the arm and the motor is activated to position the head holding device around the patient's head.

In another known cephalometric x-ray system, the equipment is mounted in a fixed position on a wall and a chair for the patient is positioned in line with the head holder. The chair is motorized to move vertically to the proper position depending on the sitting height of the patient.

There are essentially identical drawbacks to both of these prior art systems. First, both are quite expensive. The moveable version requires a large arm and the controls to move the same. The fixed version requires the expensive moveable chair. Moreover, both versions tie up a significant amount of space in the physician's or dentist's office. The x-ray equipment takes up more than five feet of wall space and extends out into the room a significant distance—which distance is even more compounded when the chair is required. Such is a particular waste of space when it is considered that the equipment is only used occasionally, as is the case with most dentists, for example, who must have the equipment for, but only occasionally use or need, full head or cephalometric x-rays. Thus, during the vast majority of the time, these expensive devices are merely wasting valuable office space.

Therefore, the need exists for inexpensive x-ray systems, such as cephalometric x-ray systems, which are conveniently operated and which do not utilize excessive space when not in use.

DISCLOSURE OF THE INVENTION

It is thus an object of the present invention to provide an x-ray system which is readily positionable with respect to the patient to be x-rayed.

It is another object of the present invention to provide an x-ray system, as above, in which the x-ray source is readily aligned with the patient and the film.

It is a further object of the present invention to provide an x-ray system, as above, in which the components thereof are adjustably movable along a wall and yet readily and easily locked in place.

It is yet another object of the present invention to provide an x-ray system, as above, in which the majority of components thereof may be removed from their position on a wall and stored when not in use so as not to waste valuable floor space.

It is an additional object of the present invention to provide an x-ray system, as above, which is inexpensive to own and easy to operate.

These and other objects of the present invention, as well as the advantages over existing prior art forms, which will become apparent from the description to follow, are accomplished by the invention hereinafter described and claimed.

In general, an x-ray system made in accordance with the concepts of the present invention includes a pair of tracks mounted on a wall in a spaced, parallel relationship. Each track carries a traveller assembly moveable thereon. One traveller assembly carries an x-ray source positioner and the other carries an x-ray receiver. Means are provided to align the traveller assemblies and, once aligned, means are provided to hold them in place on the tracks.

A preferred exemplary x-ray system incorporating the concepts of the present invention is shown by way of example in the accompanying drawings without attempting to show all the various forms and modifications in which the invention might be embodied, the invention being measured by the appended claims and not by the details of the specification.

PREFERRED EMBODIMENT FOR CARRYING OUT THE INVENTION

Figure 1:
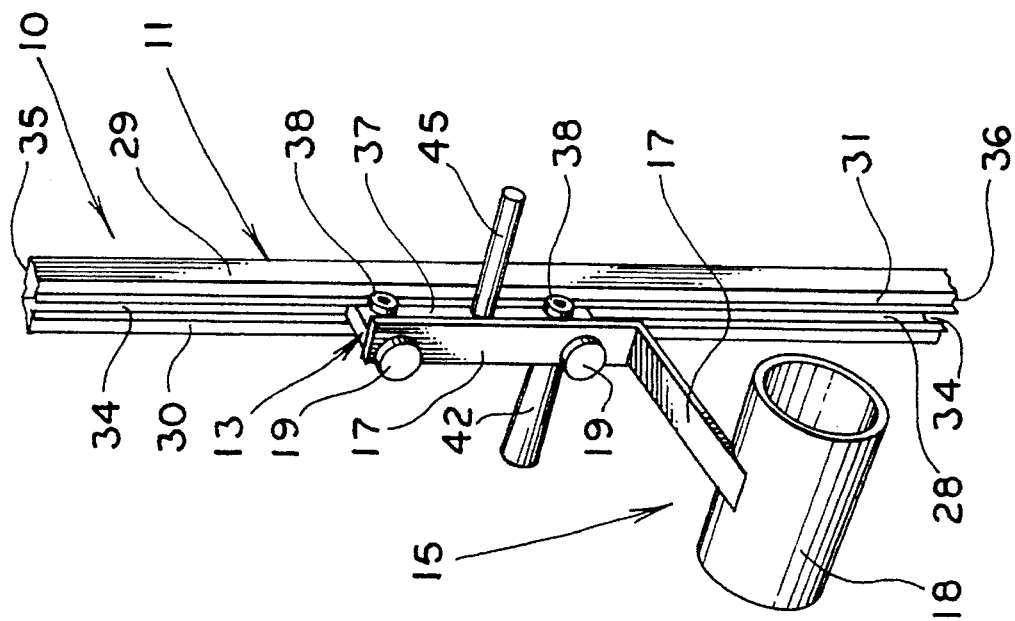
FIG. 1 is a fragmented perspective view of an x-ray system made in accordance with the present invention which shows tracks mounted on a wall, travellers positioned in the tracks and x-ray equipment, somewhat schematically shown, carried by the travellers.
Figure 1:
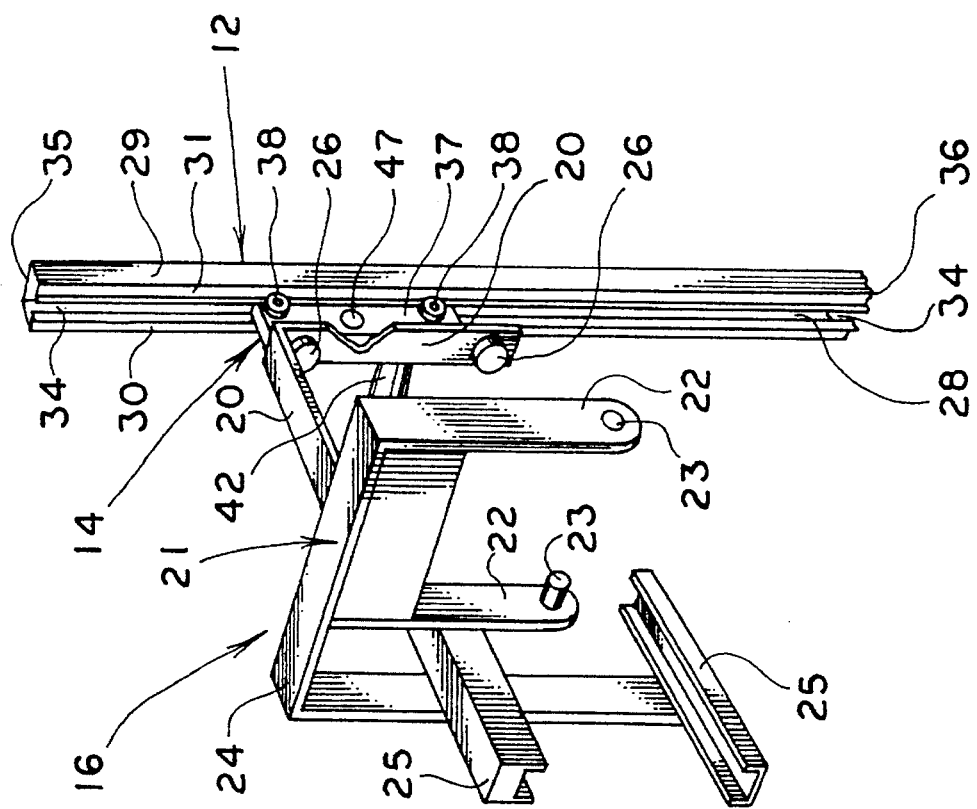

An x-ray system made in accordance with the concepts of the present invention is indicated generally by the numeral 10 in FIG. 1 and includes a pair of tracks generally indicated by the numerals 11 and 12 and mounted in a vertical and parallel relationship on a wall. As will hereinafter become evident, tracks 11 and 12 are of a length, and are mounted at a height, so as to extend through the normal range of human heights.

System 10 also includes a traveller assembly generally indicated by the numeral 13 and removably carried by track 11, and a traveller assembly generally indicated by the numeral 14 and removably carried by track 12. With one exception, to be hereinafter described, traveller assemblies 13 and 14 are identical in construction, but serve different functions. Traveller assembly 13 is adapted to carry x-ray source equipment, schematically shown and generally indicated by the numeral 15 in FIG. 1, and traveller assembly 14 is adapted to carry x-ray receiving and patient locating equipment, schematically shown and generally indicated by the numeral 16 in FIG. 1.

X-ray source equipment 15 includes an L-shaped bracket 17 which carries a conventional x-ray tube 18 at a predetermined lateral distance away from track 11 and the wall. X-ray tube 18 is adapted to receive the conventional x-ray source (not shown). Bracket 17 may be attached to traveller assembly 13, as by thumb bolts 19.

X-ray receiving and patient locating equipment 16 includes an L-shaped bracket 20 which carries, in the instance of cephalometric x-rays, a U-shaped head positioning device 21 having downwardly directed branches 22 each carrying opposed ear pins 23. In practice, a patient's head is positioned between branches 22 with the patient's ears aligned with pins 23. The patient is then in the proper position for a cephalometric x-ray. It should be, or will become evident, however, that system 10 could be utilized to x-ray other portions of the anatomy, the vertical position of which varies depending on the size of the patient.

Equipment 16 also includes another L-shaped bracket 24 which can be carried by bracket 20. Bracket 24 carries opposed film holding plates 25 or like devices to hold the x-ray film adjacent to the patient's head. In practice, the film should be about five feet from the x-ray source so that tracks 11 and 12 are spaced from each other such that when bracket 20 is attached to traveller assembly 14, as by thumb bolts 26, film holding plates 25 are about five feet from x-ray tube 18.

Figure 2:
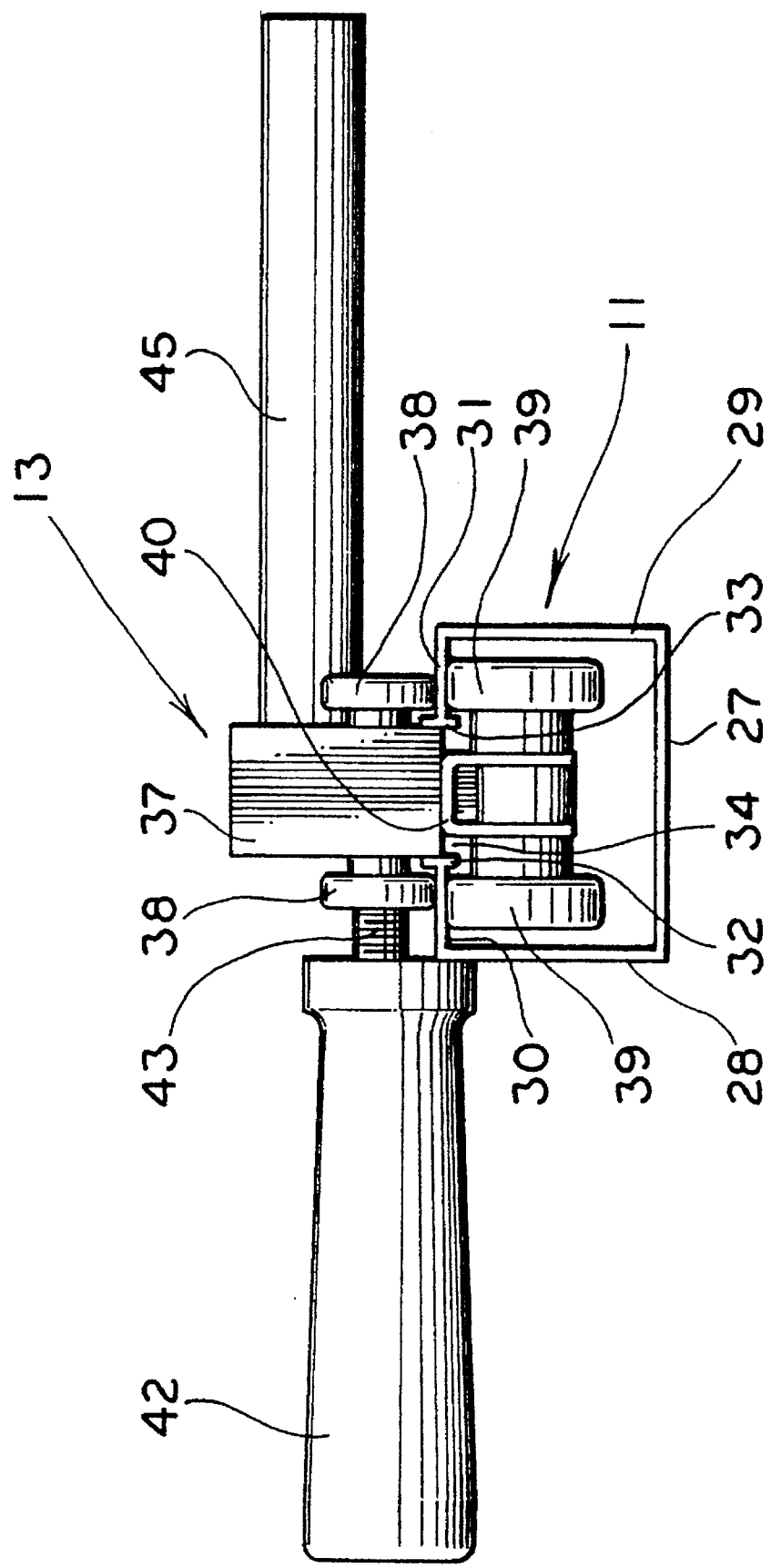
FIG. 2 is an end elevational view of a traveller in a track as shown in FIG. 1.

The configuration of identical tracks 11 and 12 is best shown in FIG. 2 with reference to an end view of track 11. Track 11 is a box-like structure having a rear wall 27 adapted to be attached to the wall of the room in any suitable fashion and side walls 28 and 29 extending laterally away from rear wall 27 and the wall of the room in which system 10 is installed. Track rails 30 and 31 are formed at the inner ends of walls 28 and 29, respectively, and extend toward each other and generally parallel to rear wall 27. Rails 30 and 31 terminate as opposed, spaced, guide flanges 32 and 33, respectively, which are generally parallel to side walls 28 and 29. Tracks 11 and 12 thus have a partially open front face, as at 34, between flanges 32 and 33. In addition, tracks 11 and 12 are each open at their top 35 and bottom 36 so that travellers 13 and 14 may be readily removed therefrom as will be hereinafter described.

Figure 3:
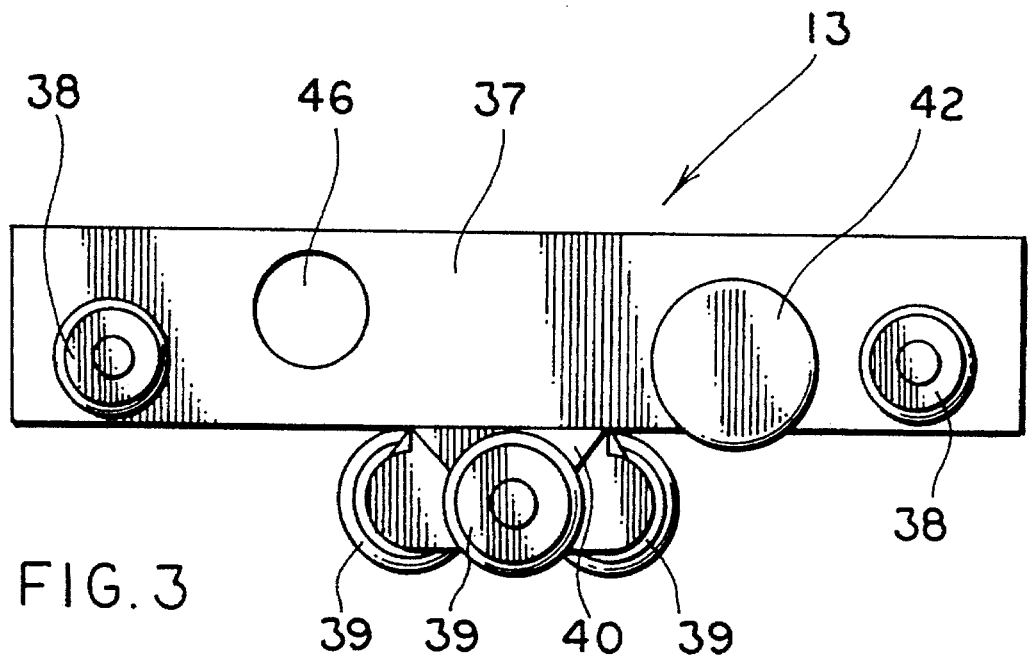
FIG. 3 is a side elevational view of a traveller of FIG. 1.
Figure 4:
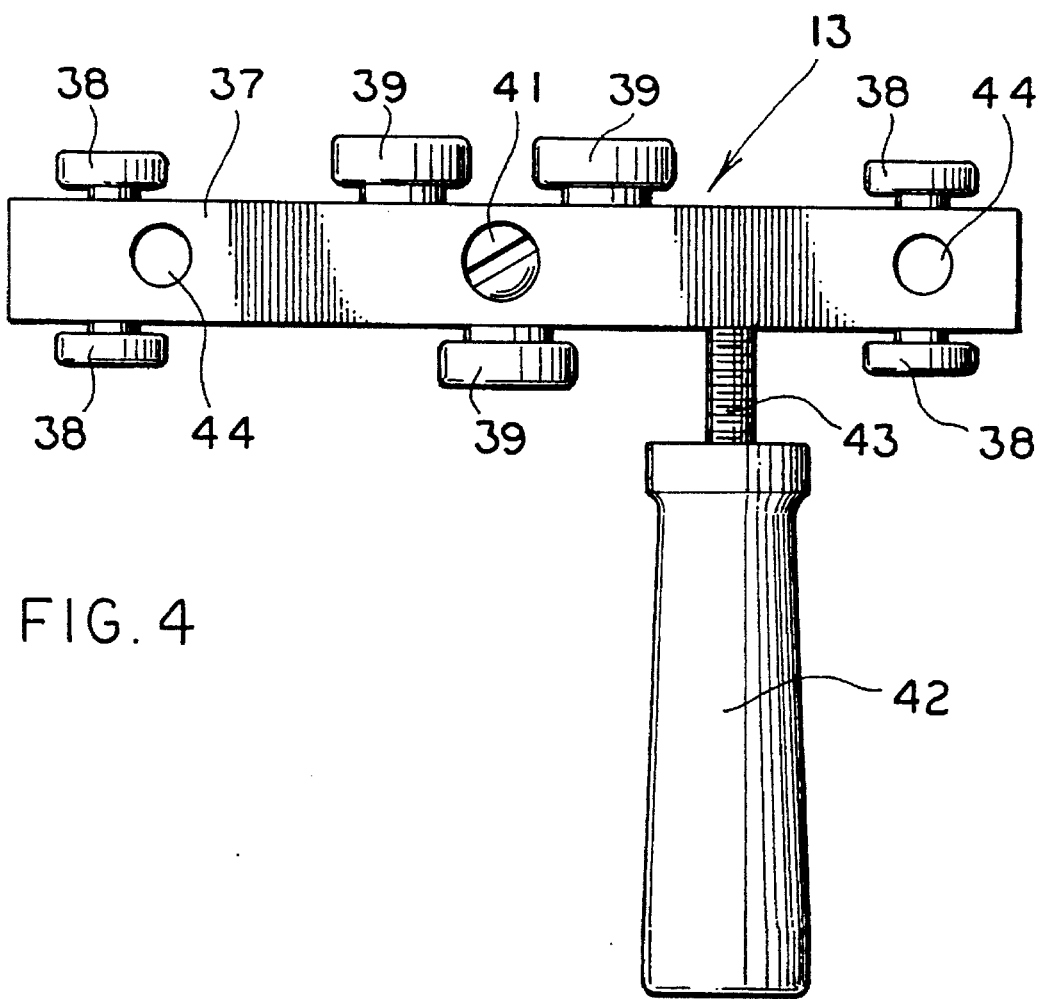
FIG. 4 is a front elevational view of the traveller of FIG. 3.

With particular reference to FIGS. 2–4, traveller assembly 13 is shown therein, and traveller assemblies 13 and 14 will now be described, keeping in mind that, as previously indicated, traveller assemblies 13 and 14, with one exception, are identical. Traveller assemblies 13 and 14 thus each include a main body portion 37 generally in the shape of a rectangular block. A pair of rollers 38 is carried near each end of body portion 37 and, as shown in FIG. 2, rollers 38 are adapted to ride on the outside of rails 30 and 31. A grouping of three rollers 39 is positioned to ride on the inside of rails 30 and 31, although two opposed or four opposed rollers would operate just as well. Rollers 39 are carried by a bogie frame 40 which is attached, as by fastener 41 (FIG. 4), to body portion 37.

Rollers 38 and 39 are preferably made of a nylon material and are laterally spaced from each other a distance slightly less than the thickness of rails 30 and 31 as shown in FIG. 2. Travellers 13 and 14 are positioned on tracks 11 and 12 by threading rollers 39 through either open end 35 or 36 thereof with rails 30 and 31 between rollers 38 and 39 as shown in FIG. 2. As such, there is a fairly tight friction fit as rails 30 and 31 are engaged by rollers 38 and 39. Moreover, when so positioned, body portion 37 is relatively tightly received between guide flanges 32 and 33 which further stabilizes travellers 13 and 14 on tracks 11 and 12, respectively.

Nevertheless, with the assistance of a handle 42, the frictional fit between rollers 38 and 39 and rails 30 and 31 may be overcome, and travellers 13 and 14 may be manually positioned at any point along tracks 11 and 12, respectively. Handle 42 has a threaded shaft 43 which is received by body portion 37 of each traveller 13 and 14. When the desired vertical position of travellers 13 or 14 is reached, its handle 42 may be tightened so that it frictionally engages side wall 28 of tracks 11 and 12 as shown in FIG. 2.

Body portion 37 of travellers 13 and 14 also carries the x-ray receiving and patient locating equipment 16, respectively. To that end, body portion 37 is provided with threaded openings 44 (FIG. 4) to receive thumb bolts 19 and 26.

Travellers 13 and 14 each carry a different component of an alignment system which represents the only structural difference between travellers 13 and 14. Thus, traveller 13 is designed to carry an alignment source, which can be in the form of an optical or laser beam transmitter 45 carried by body portion 37 as shown in FIGS. 1 and 2. While such can be a permanent part of traveller 13, transmitter 45 can be in the form of the conventional portable laser pointer used, for example, by speakers during lectures. As such, it can be removably positioned in an aperture 46 (FIG. 3), extending through body portion 37, as desired. Traveller 14, however, is not provided with a transmitter 45 but rather has a receiver in the form of a target 47 (FIG. 1) to receive the beam of transmitter 45 to align travellers 13 and 14. Target 47 is at the same position of its body portion 37 as is the transmitter 45 of its body portion 37. Of course, other optical alignment systems could be substituted for laser beam transmitter 45 without departing from the spirit of the present invention. For example, simple ruler-like calibrations could be imprinted on tracks 11 and 12 for the positioning of travellers 13 and 14. Of course, such would require that tracks 11 and 12 be precisely positioned at the same height on the wall whereas, in the optical alignment system just described, such would not be mandatory.

In the operation and utilization of system 10, traveller 14, having equipment 16 attached thereto, is positioned onto track 12 and moved by grasping handle 42 until it is at the proper height: that is, with the patient standing adjacent to track 12 and the patient's ears aligned with pins 23. Then handle 42 is tightened against track side wall 28 to hold traveller 14 at the desired height and assure that it does not fall, under the weight of equipment 16, out of track 14. Then traveller 13, having equipment 15 attached thereto, is positioned in track 11 and by means of handle 42, and with beam transmitter activated, it is moved along track 11 until the beam is squarely aligned with target 47 at which time handle 42 can be tightened against track side wall 28 to hold it in place. At this time, x-ray tube 18 is properly aligned with the patient and the x-ray may be taken.

When the system 10 is no longer needed, handles 42 may be loosened and travellers 13 and 14, and the equipment 15 and 16 that they are carrying, can be removed through either top openings 35 or bottom openings 36 of tracks 11 and 12, and the system can be stored in a convenient place. As such, it is not taking up space in the room adjacent to tracks 11 and 12 which can permanently remain on the wall. Or, if desired, the travellers 13 and 14 may be left on tracks 11 and 12 and the x-ray equipment merely removed therefrom, for storage, by loosening thumb bolts 19 and 26.

It should thus be apparent that a system constructed and operated as described herein substantially improves the art and otherwise accomplishes the objects of the present invention.

We claim:

1. An x-ray system adapted to be mounted on one wall of a room comprising a first track adapted to be mounted on the wall, a second track adapted to be mounted on the wall spaced from and parallel to said first track, first traveller means moveable on and carried by only said first track and adapted to carry an x-ray source positioner, second traveller means moveable on and carried by only said second track and adapted to carry an x-ray receiver, means to align said first and second traveller means, and means to hold said first and second traveller means at their aligned position.

2. An x-ray system according to claim 1 wherein said means to hold also facilitates movement of said traveller means on said tracks.

3. An x-ray system according to claim 2 wherein said means to hold includes a handle carried by each said traveller means, and means to vary the position of each said handle relative to each said traveller means.

4. An x-ray system according to claim 3 wherein said means to vary includes a threaded shaft carried by each said handle and received by each said traveller means.

5. An x-ray system according to claim 1 wherein said means to align includes an optical source carried by said first traveller means and optical receiving means carried by said second traveller means.

6. An x-ray system according to claim 5 wherein said optical source is removedly carried by said first traveller means.

7. An x-ray system according to claim 5 wherein said receiving means is a target positioned on said second traveller means.

8. An x-ray system according to claim 1 wherein said second traveller means is also adapted to carry patient alignment equipment between the x-ray source positioner and the x-ray receiver.

9. An x-ray system according to claim 1 wherein the x-ray source positioner is removably carried by said first traveller means and the x-ray receiver is removably carried by said second traveller means.

10. An x-ray system adapted to be mounted on one wall of a room comprising a first track adapted to be mounted on the wall, a second track adapted to be mounted on the wall spaced from and parallel to said first track, first traveller means moveable on said first track and adapted to carry an x-ray source positioner, second traveller means moveable on said second track and adapted to carry an x-ray receiver, at least one end of each said track being open so that each said traveller means may be removed from each said track, means to align said first and second traveller means, and means to hold said first and second traveller means at their aligned position.

11. An x-ray system adapted to be mounted on one wall of a room comprising a first track adapted to be mounted on the wall, a second track adapted to be mounted on the wall spaced from and parallel to said first track, first traveller means moveable on said first track and adapted to carry an x-ray source positioner, second traveller means moveable on said second track and adapted to carry an x-ray receiver, each said traveller means including a body portion and spaced, opposed rollers carried by each said body portion, each said track having rails positioned in the space between said opposed rollers, means to align said first and second traveller means, and means to hold said first and second traveller means at their aligned position.

12. An x-ray system according to claim 11 wherein the space between said opposed rollers is less than the thickness of said rails so that said rollers frictionally engage said rails.

13. An x-ray system according to claim 11, each said track further including opposed guide flanges positioned on said rails, said body portion of each said traveller means being positioned between each of said opposed guide flanges.

14. An x-ray system adapted to be mounted on one wall of a room comprising a first longitudinally extending track adapted to be mounted on the wall; a second longitudinally extending track adapted to be mounted on the wall spaced from and parallel to said first track; each said track having at least one open end; first traveller means moveable on said first track, removable therefrom through said open end, and adapted to carry x-ray equipment; and second traveller means moveable on said second track, removable therefrom through said open end, and adapted to carry other x-ray equipment.

15. An x-ray system according to claim 14 further comprising means to align said first and second traveller means.

16. An x-ray system according to claim 14 further comprising means to hold each said traveller means at a desired position on each said track means.

17. An x-ray system according to claim 14 further comprising handle means carried by each said traveller means to assist in moving each said traveller means in each such track.

18. An x-ray system according to claim 17 wherein each said handle means is moveable relative to each said traveller means and each such track so as to engage each said track and hold each said traveller means at a desired position on each said track.

19. An x-ray system according to claim 14 wherein each said track includes rail members, and each said traveller means includes a body portion and spaced, opposed rollers carried by each said body portion, said rollers being positioned on each side of said rail members.

20. An x-ray system according to claim 19 wherein the space between said rollers is less than the thickness of said rails so that said rollers frictionally engage said rails.

* * * * *